(12) United States Patent
Feistel

(10) Patent No.: US 10,585,101 B2
(45) Date of Patent: Mar. 10, 2020

(54) PROSTATIC LIQUID BIOPSY FOR THE DETECTION OF PROSTATE CANCER AND BENIGN PROSTATIC HYPERPLASIA

(71) Applicant: WAVESENSE, INC., Irvine, CA (US)

(72) Inventor: Christopher Feistel, Irvine, CA (US)

(73) Assignee: WAVESENSE, INC., Irvine, CA (US)

( * ) Notice: Subject to any disclaimer, the term of this patent is extended or adjusted under 35 U.S.C. 154(b) by 767 days.

(21) Appl. No.: 15/066,910

(22) Filed: Mar. 10, 2016

(65) Prior Publication Data

US 2017/0261510 A1   Sep. 14, 2017

(51) Int. Cl.
*A61B 5/00* (2006.01)
*G01N 33/574* (2006.01)
*A61K 31/58* (2006.01)
*C12Q 1/6886* (2018.01)
(Continued)

(52) U.S. Cl.
CPC ....... *G01N 33/57434* (2013.01); *A61K 31/58* (2013.01); *A61B 2017/00274* (2013.01); *A61B 2018/00547* (2013.01); *C12Q 1/6886* (2013.01)

(58) Field of Classification Search
CPC ........ G01N 33/57434; G01N 2800/342; A61B 2017/00274; A61B 2018/00547; A61K 31/58; C12Q 1/6886
See application file for complete search history.

(56) References Cited

U.S. PATENT DOCUMENTS 5,496,271 A   3/1996 Burton et al.
5,496,556 A   3/1996 Johnson
(Continued)

FOREIGN PATENT DOCUMENTS

CN   2294728       10/1998
WO   2003011114   2/2003

OTHER PUBLICATIONS http://www.cancer.gov/types/prostate/understanding-prostate-changes "Understanding Prostate Changes: A Health Guide for Men; National Cancer Institute"; downloaded Jan. 26, 2016.
(Continued)

*Primary Examiner* — Max F Hindenburg
(74) *Attorney, Agent, or Firm* — Stetina Brunda Garred and Brucker

(57) ABSTRACT

Disclosed are methods to induce dislodgement of target prostatic cells from the prostate organ, collecting said cells, and subsequently examining the cell population. Such methods comprise the administration of an agent that facilitates the dislodgement of the target cells from within the prostate, which then migrate into the urethra. Exemplary agents include 5 alpha-reductase inhibitors. The cells induced to pass into the urethra are then collected non-invasively, such as through urine or semen samples. Such collection is further strategically calculated relative the administration of the agent so as to maximize the sample collection of the target cells of interest. The exfoliated prostatic epithelial cells are subsequently utilized for purposes such as detecting prostate cancer, predicting/measuring prostate tumor susceptibility to drug regimes, active surveillance of patients whose prostate biopsy results are negative, but continue to exhibit symptoms consistent with prostate cancer, and identifying false positive results associated with biomarker assays.

21 Claims, 3 Drawing Sheets

(51) Int. Cl.
    A61B 17/00    (2006.01)
    A61B 18/00    (2006.01)

(56) References Cited

U.S. PATENT DOCUMENTS

| | | | |
|---|---|---|---|
| 5,912,135 A * | 6/1999 | Luderer | G01N 33/68 |
| | | | 435/7.4 |
| 6,054,341 A | 4/2000 | Kim | |
| 6,054,432 A | 4/2000 | Engel et al. | |
| 6,054,314 A | 8/2000 | Kim | |
| 6,300,060 B1 | 10/2001 | Kantoff et al. | |
| 8,374,702 B2 | 2/2013 | Mon et al. | |
| 8,945,482 B2 | 2/2015 | Mitragotri | |
| 2002/0026209 A1 | 2/2002 | Hung | |
| 2004/0230316 A1 | 11/2004 | Cioanta et al. | |
| 2005/0054994 A1 | 2/2005 | Cioanta et al. | |
| 2005/0238577 A1 | 10/2005 | Hellerstein | |
| 2006/0194230 A1* | 8/2006 | Levitt | C12Q 1/6883 |
| | | | 435/6.14 |
| 2007/0103809 A1 | 5/2007 | Lee et al. | |
| 2009/0263799 A1 | 10/2009 | Smith et al. | |
| 2011/0295161 A1 | 3/2011 | Chopra et al. | |
| 2011/0208022 A1 | 8/2011 | Brawer et al. | |
| 2011/0270366 A1 | 11/2011 | Mahon et al. | |
| 2015/0218646 A1* | 8/2015 | Haince | C12Q 1/6886 |
| | | | 506/2 |

OTHER PUBLICATIONS http://www.cancer.org/acs/groups/cid/documents/webcontent/003134-pdf.pdf Prostate Cancer; downloaded Jan. 26, 2016.

http://globocan.larc.fr/Pages/fact_sheets_cancer.aspx Prostate Cancer Estimated Incidence, Mortality and Prevalence Worldwide in 2012; downloaded Jan. 26, 2016.

Presti, Jr. MD, Joseph C.; Prostate Biopsy: Current Status and Limitations; Reviews in Urology; vol. 9 No. 3; 2007; p. 93-98; Department of Urology, Stanford University School of Medicine, Stanford, California.

Shariat, MD, Shahrokh F. et al.; Using Biopsy to Detect Prostate Cancer; Rev Urol: / 2008 Fall; 10(4); 262-280; http://www.nchi.nlm.nih.gov/pmc/articles/PMC2615104/.

Taneja, MD, Samir S.; White Paper: AUA/Optimal Techniques of Prostate Biopsy and Specimen Handling; American Urological Association, Inc.; 29 pages.

Chin, MD, Arnold I. et al.; Is Repeat Biopsy for Isolated High-Grade Prostatic Intraepithelial Neoplasia Necessary?; Reviews in Urology; vol. 9 No. 3; 2007; p. 124-131.

Obek, Can et al.; Core Length in Prostate Biopsy: Size Matters; Journal of Urology; Vo. 187, pp. 2051-2055; Jun. 2012; USA.

Jones, MD, Facs, Stephen J.; Managing Patients Following a Negative Prostate Biopsy; 12 pages; downloaded Jan. 19, 2016; http://www.renalandurologynews.com/managing-patients-following-a-negative-prostate-biopsy/printarticle/195898/.

Mustafa, Mahmoud Othman et al.; When prostate cancer remains undetectable: The dilemma; Turkish Journal of Urology 2015; 41(1); 32-38.

http://www.uspreventiveservicetaskforce.org/Page?Document?Recommend...tate-cancer-screening#table-psa-based-screening-for-prostate-cancer downloaded Jan. 21, 2016 Final Recommendation Statement: Prostate Cancer: Screening, May 2012.

Shyamala, K. et al.; Risk of tumor cell seeding through biopsy and aspiration cytology; Journal of International Society of Preventive & Community Dentistry; Jan.-Apr. 2014; 4(1): 5-11. http://www.ncbi.nim.nih.gov/pmc/articles/PMC4015162/?report=printable.

Volanis, D. et al.; Incidence of needle-tract seeding following prostate biopsy for suspected cancer: a review of the literature; BJU Int.; May 2015; 115(5); 698-704.

Gonzales, MD, Chris M. et al. AUA/SUNA White Paper on the Incidence, Prevention and Treatment of Complications Related to Prostate Needle Biopsy; American Urological Association, Inc.; 2012; pp. 1-23.

Truong, Matthew et al.; Towards the Detection of Prostate Cancer in Urine: A Critical Analysis; Journal of Urology; Feb. 2013; 189(2); 4220429.

Velonas, Vicki M. et al.; Current Status of Biomarkers for Prostate Cancer; International Journal of Molecular Sciences; Jun. 2013; 14(6); 11034-11060. http://www.ncbi.nim.nih.gov/pmc/articles/PMC3709717/.

Coulture, ML et al.; Abstratc: The isolation and identification of exfoliated prostate cells from human semen; Acta Cytol; May-Jun. 1980; 24(3): 262-267. http://www.ncbi.nim.nih.gov/pubmed/6157292.

Barren, III, Robert J., et al.; Method for Identifying Prostate Cells in Semen Using Flow Cytometry; The Prostate 36:181-188; 1998 Wiley-Liss, Inc.

Nakai, Yasushi. et al.; Photodynamic diagnosis of shed prostate cancer cells in voided urine treated with 5-aminolevulinic acid; BioMed Central: Urology 2014; 14:59; http://www.biomedcentral.com/1471-2490/14/59.

Tyler, KL, et al.; Abstract: Morphologic features of prostatic adenocarcinoma on ThinPrep urinary cytology; 2 pages downloaded Jan. 28, 2016 http://www.ncbi.nim.nih.gov/pubmed/20146303.

Khan, Naghma, et al.; Abstract: Apoptosis by dietary agents for prevention and treatment of prostate cancer; pub. Endocr Relat Cancer; Mar. 2010; 17(1); R39-R52.

Thompson, Ian M. et al.; Long-term Survival of Participants in the Prostate Cancer Prevention Trial; The New England Journal of Medicine; Aug. 15, 2013; vol. 369; No. 7; p. 603-610.

Bostwick, David g. et al; High-grade prostatic intraepithelial neoplasia; Modem Pathology 2004; 17, 360-379. www.modernpathology.org.

Kim, Hyung L. et al.; Prevalence of High-trade Prostatic Intraepithelial Neoplasia and Its Relationship to Serum Prostate Specific Antigen; Clinical Urology; vol. 28(5); 413-417; Sep.-Oct. 2002; p. 413-417.

Wikipedia the Free Encyclopedia; 5-alpha-reductase inhibitor. https://en.wikipedia.org/wiki/5-alpha-reductase_inhibitor.

Pedersen, Elisabeth A., et al.; The prostate cancer bone marrow niche: more than just 'fertile soil'; Asian Journal of Andrology; May 2012; 14(3); 423-427.

Murray, N.P., et al.; Presence of prostate cells in bone marrow biopsies as a sign of micrometastasis in cancer patients; Oncology Reports 21: 571-575; 2009; Columbia University Medical Center, New York, NY, USA.

Ross, Robert W., et al.; Predictors of prostate cancer tissue acquisition by an undirected core bone marrow biopsy in metastatic castration-resistant prostate cancer—a Cancer and Leukemia Group B Study; Clinical Cancer Research 2005; 11:8109-8113.

http://www.cancer.gov/types/prostate/research/finasteride-reduces-low-grade National Cancer Institute: Finasteride Reduces the Risk of Low-Grade Prostate Cancer in Men 55 and Older; 3 pages.

Kearney, Michael C. et al.; Clinical Predictors in the use of Finasteride for Control of Gross Hematuria Due to Benign Prostatic Hyperplasia; The Journal of Urology; vol. 167; 2489-2491; Jun. 2002, USA.

Hennenfent, MD, Bradley R., et al.; Repetitive Prostatic Massage and Drug Therapy as an Alternative to Transurethral Resection of the Prostate; MedGenMed 2006; 8(4): 19; pub. on line Oct. 25, 2006; 11 pages.

Young, Lee W., PCT International Search Report & Written Opinion, dated May 26, 2017, 7 pages.

Sutton et al., Finasteride Targets Prostate Vascularity by Inducing Apoptosis and Inhibiting Cell Adhesion of Benign and Malignant Prostate Cells, The Prostate, Aug. 1, 2006, vol. 66, pp. 1194-1202, p. 1194.

Wikipedia, Ejaculatory duct, Aug. 14, 2015, p. 1/2, Retrieved on Apr. 24, 2017 from <https://en.wikipedia.org/wiki/Ejaculatory_duct>.

Trost, et al; Side Effects of 5-Alpha Reductase Inhibitors A Comprehensive Review; Sexual Medicine Reviews; May 1, 2013, 16 pages; vol. 1, No. 1.

Anonymous; Ejaculatory_duct, Wikipedia, Aug. 14, 2015; 2 pages; [retrieved Oct. 11, 2017]; Retrieved from the Internet: https://en.wikipedia.org/wiki/Ejaculatory_duct.

(56) References Cited

OTHER PUBLICATIONS

Sutton, et al; Finasteride Targets Prostate Vascularity by Inducing Apoptosis and Inhibiting Cell Adhesion of Benign and Malignant Prostate Cells; The Prostate, Jan. 1, 2016; 9 pages, vol. 66, No. 11.
Boiangiu, Clara, Supplementary European Search Report, dated Oct. 18, 2019, 13 pages, Munich, Germany.

* cited by examiner

PROSTATIC LIQUID BIOPSY FOR THE DETECTION OF PROSTATE CANCER AND BENIGN PROSTATIC HYPERPLASIA

CROSS-REFERENCE TO RELATED APPLICATIONS

Not Applicable

STATEMENT RE: FEDERALLY SPONSORED RESEARCH/DEVELOPMENT

Not Applicable

BACKGROUND

Prostate cancer is the most common cancer found in men and it is the second leading cause of death among men who die from cancer. By the age of 50, very few men have symptoms of prostate cancer, yet some precancerous or cancer cells may be present. More than half of all American men have some cancer in their prostate glands by the age of 80. Most of these cancers never pose a problem. See, National Cancer Institute Understanding Prostate Changes: A Health Guide for Men (http://wwwdotcancerdotgov/types/prostate/understanding-prostate-changes) current website guide Jan. 26, 2016. The American Cancer Society's estimates for prostate cancer in the United States for 2015 are approximately 220,800 new cases of prostate cancer; and 27,540 deaths from prostate cancer. See, American Cancer Society Prostate Cancer Guide (Ref: http://wwwdotcancerdotorg/acs/groups/cid/documents/webcontent/003134-pdf-.pdf.) In 2012, the World Health Organization (WHO) estimated that 1.1 million men worldwide were diagnosed with prostate cancer (Ref: World Health Organization Prostate Cancer Fact Sheet. See, GloboCan 2012: Estimated Cancer Incidence, Mortality and Prevalence Worldwide in 2012. (http://globocandotiarcdotfr/Pages/fact_sheets_cancer.aspx)). That number was 15% of all cancers diagnosed in men. Also in 2012, WHO estimated that there were 307,000 deaths representing 6.6% of total men cancer deaths.

To illustrate such disease, there is depicted, in FIGS. 1 and 2, in cross-sectional view, a prostate 10 in proximity to other organs and anatomical structures, and how a cancerous growth within the prostate progresses through Stages I, II, III and IV. As shown in FIG. 1, the prostate is located just below the bladder 40 and in front of the rectum 50. The prostate 10 further surrounds a portion of the urethra 60 and further produces seminal fluid that nourishes and transports sperm as part of the male reproductive system. The progression of prostate cancer, like other forms of cancer, is characterized by four categories of staging that describe the local extent of a prostate tumor, ranging from Stage I or T1 to Stage IV or T4. With respect to Stage I, the tumor 20 typically cannot be felt or even seen with imaging equipment, such as transrectal ultrasound. Although highly ideal, the detection of cancer at such stage is considered almost accidental and is typically incidental to a separate transurethral resection of the prostate (TURP). Detection at such stage can also occur by needle biopsy performed as a result in increased prostate specific antigen (PSA), discussed more fully below.

Stage II is characterized as becoming enlarged to the point where the cancer 20 can be felt per a digital rectal exam (DRE) or can be seen with imaging such as transrectal ultrasound. The cancer 20 at such stage however, continues to be confined to the prostate gland 10.

In Stage III, the cancer 20 has grown outside of the prostate 10 and may have further grown into the seminal vesicle 30. In Stage IV, the cancer 20 has grown into tissue adjacent to the prostate (i.e., other than the seminal vesicles) and can extend into such structures such as the urethral sphincter, rectum 50, bladder 40 and/or the wall of the pelvis.

The treatment of prostate cancer can vary significantly depending on factors such as how fast the cancer is growing, how much it has spread, the patient's overall health, and the benefits and potential side effects of treatment. As is true for virtually all types of cancers, early detection is always preferred, with the treatment options available having substantially fewer side effects and significantly greater patient outcome compared to detection at later stages. Given the anatomical positioning of the prostate, however, coupled with numerous drawbacks associated with the accurate diagnosis of prostate cancer, the ability to detect prostate cancer at its earliest stages is elusive and well-known to result in the implementation of harmful, sub-optimal care, as discussed below.

I. Disadvantages Associated with Current Prostate Cancer Screening Methods

Management and treatment of prostate cancer is limited by access to an adequate sample of prostate tissue. See, Presti, J. Prostate Biopsy: Current Status and Limitations. Rev Urol. 2007, Summer, 9(3): 93-98. In this regard, the definitive diagnosis of prostate cancer is hampered by the limitations of acquiring prostate gland tissue using an invasive surgical procedure known as a prostate core needle biopsy. See, Shariat et. al. Using Biopsy to Detect Prostate Cancer. Reviews in Urology, 2008 Fall; 10(4): 262-280; and Taneja, et al. AUA/Optimal Techniques of Prostate Biopsy and Specimen Handling: White Paper for the American Urological Association, Inc. in https://wwwdotauanetdotorg/common/pdf/education/clinical-guidance/Prostate-Biopsy-WhitePaper.pdf as of Jan. 26, 2016. Specifically, such biopsy procedure is typically performed by a physician using transrectal ultrasound to visualize the prostate gland while a hollow needle is inserted through the wall of the rectum into the prostate gland. As the needle penetrates prostate tissue, a core of tissue forms inside the needle. When this needle is retracted from the prostate, the tissue core is expelled from the needle and mounted on a microscope slide for examination. Only tissue along the path of the needle can be examined. This procedure is repeated between 8 to 18 times (12 on average) to acquire tissue biopsy samples from multiple regions of the prostate. Local anesthesia is typically injected into the region adjoining the prostate to reduce pain associated with the biopsy procedure. Antibiotics are also administered to reduce the high infection risk associated with wounds near the rectum.

Based upon estimates of 1.3 million prostate biopsy procedures performed in the United States and an average of 12 cores per biopsy, approximately 15 million core biopsy specimens are collected and examined in the United States annually. More than 10 million (~70%) of these biopsies are determined to be negative for prostate cancer. See, Chin et al., Is Repeat Biopsy for Isolated High-Grade Prostatic Intraepithelial Neoplasia Necessary? Rev Urology 2007; 9(3): 124-131. Due to physical limitations of the prostate core biopsy, there are more that 3 million false negative biopsies reported presumably resulting from failure of the needle to pass through cancer tissue. Many men with negative biopsy results are placed on active surveillance and will undergo second and third biopsy procedures due to persistent indications for repeat biopsy. As is recognized, a key cause for this excessive false negative rate is the limited needle path inherent to core needle biopsy procedures.

When the prostate core biopsy procedure is examined closely, it is apparent that small tumors are easily missed and will continue to flourish undetected and untreated. Also contributing to this failure to detect tumors is the small percentage of prostate tissue sampled by the biopsy procedure. The majority of prostate core biopsies are performed using an 18 gauge needle. Such biopsy needle produces a prostate tissue core with a maximum diameter of 0.84 mm and a typical length of 12 mm. See, Obek et al., Core length in prostate biopsy: size matters. J Urol. 2012 June; 187(6): 2015-5. An average prostate tissue volume of 8 microliters is acquired with each core. Based on an average of 12 cores per procedure, an estimated total of 0.096 milliliters of prostate tissue is acquired per procedure. See, Mustafa et al., When prostate cancer remains undetectable: The dilemma, Turkish J Urol 2015; 41(1): 32-8. Approximately 8 microliters per core×12 cores=96 microliters (0.096 mL). Adult male prostate tissue volumes, however, range between 25 and 50 mL. Thus, the percentage of total prostate tissue volume acquired by biopsy ranges from 0.384% to 0.2% of total prostate volume and after mounting and sectioning the cores for microscopic examination, less than 0.01% of the whole prostate tissue volume is examined.

Moreover, the biopsy procedure accesses the prostate through the rectum whereby the posterior prostate is most easily accessible to the biopsy apparatus. Hence a sampling bias exists and anterior tumors (located anterior to the urethra) require significantly more biopsy sessions than posterior tumors. See, Jones, Managing Patients Following a Negative Prostate Biopsy, Renal and Urology News 2011 Feb. 1. In this regard, and as illustrated in FIG. 5 (showing another aspect of the invention discussed herein), tumor 20 is situated in a deep, anterior position located at an opposed end where the prostate could otherwise be accessed through the rectum. As a consequence, even to the extent needle biopsies could access and detect the presence of cancerous tissue, such approach is only as effective as the entirety of the random sampling made about prostate organ, which needs to be sufficiently sampled completely thereabout rather than just not in the more easily accessed areas. Tumor 20 in FIG. 5 depicts how detecting such a tumor is problematic.

There can likewise be significant discomfort and medical risk associated with prostate core needle biopsies. Bleeding, antibiotic resistant infection/sepsis, urine retention, and tumor seeding (i.e., dislodging of tumor cells into tissue fluid or the circulation) are all well-known drawbacks associated with such procedure. See, e.g., US Preventative Services Task Force, Final Recommendation Statement Prostate Cancer: Screening, May 2012, K. Shyamala, et al., Risk of tumor cell seeding through biopsy and aspiration cytology, Journal of International Society of Preventive & Community Dentistry 2014 January-April; 4(1): 5-11); Volanis, et al., Incidence of needle-tract seeding following prostate biopsy for suspected cancer: a review of the literature, BJU Int. 2015 M; 115(5): 698-704); and Gonzales et al., AUA/SUNA White Paper on the Incidence, Prevention and Treatment of Complications Related to Prostate Needle Biopsy, American Urological Association Education and Research, Inc., 2012. Taken together, the medical risk, poor sensitivity, and patient discomfort, the prostate core biopsy procedure is a less than ideal active surveillance tool that is limited to annual or semi-annual use. Presently, there is a need for less invasive diagnostic methods to examine the prostate for the presence of prostate cancer.

As a potential diagnostic substitute, biomarkers have long been proposed as a non-invasive surveillance alternative to core needle biopsy. Specifically, non-invasive or minimally invasive diagnostic methods have been developed as indicators for a prostate core biopsy. Generally, these methods rely on detection of extracellular biomarkers present in body fluids or blood. See, Truong et al., Towards the Detection of Prostate Cancer in Urine: A Critical Analysis, J Urol. 2013 February; 189(2): 422-429. The biomarker data is typically interpreted against the result of a digital palpation through the rectum (digital rectal examine or DRE). The most common biomarker used for this purpose is prostate specific antigen (PSA). The link between prostate cancer and elevated (above normal range) levels of PSA as measured in human serum was first published in 1979. Since the discovery of PSA, many alternatives to PSA have been proposed and deployed clinically. A complete review of biomarkers for prostate cancer is disclosed in Velonas V., et al., Current Status of Biomarkers for Prostate Cancer, International Journal of Molecular Science, 2013 June; 14(6): 11034-11060, and incorporated herein by reference.

Unfortunately, despite the availability of multiple biomarkers relating to prostate cancer, none can match the unequivocal specificity of skilled examination of prostate tissue by a pathologist. Moreover, biomarker indications of prostate cancer are always confirmed by tissue biopsy prior to treatment and management of the patient and the data supporting this standard of care are overwhelming. In this regard, no biomarker has replaced PSA/DRE as the standard of care for prostate cancer surveillance and at best biomarkers serve as a surrogate for examining the cell type presumed to be associated with prostate cancer. As such, biomarkers cannot achieve specificity equivalent to interrogation of the physical prostate cell. Hence, tissue biopsy prevails as the definitive diagnostic method.

In fact, despite the belief that biomarkers may offer a less invasive method of patient management, data shows that a great deal of patient harm is associated with the use of biomarkers in patient management for prostate cancer. Along these lines, convincing evidence demonstrates that the PSA test often produces false-positive results, with reports that approximately 80% of positive PSA test results are false-positive when cutoffs between 2.5 and 4.0 µg/L are used. There is also adequate evidence that false-positive PSA test results are associated with negative psychological effects, including persistent worry about prostate cancer. Men who have a false-positive test result are more likely to have additional testing, including one or more biopsies in the following year than those who have a negative test result and over ten years, approximately 15% to 20% of men will have a PSA test result that triggers a biopsy, depending on the PSA threshold and testing interval used. Indeed, in addition to the findings discussed above, recent evidence from a randomized trial of treatment of screen-detected cancer indicates that roughly one third of men who have prostate biopsy experience pain, fever, bleeding, infection, transient urinary difficulties, or other issues requiring clinician follow-up that the men consider a "moderate or major problem" with approximately 1% requiring hospitalization.

II. Harms Related to Treatment of Screen-Detected Cancer

Adequate evidence shows that nearly 90% of men with PSA-detected prostate cancer in the United States have early treatment with surgery, radiation, or androgen deprivation therapy. Adequate evidence shows that up to 5 in 1000 men will die within 1 month of prostate cancer surgery and between 10 and 70 men will have serious complications but survive. Radiotherapy and surgery result in long-term adverse effects, including urinary incontinence and erectile dysfunction in at least 200 to 300 of 1000 men treated with these therapies. Radiotherapy is also associated with bowel dysfunction.

Some clinicians have used androgen deprivation therapy as the primary therapy for early-stage prostate cancer, particularly in older men, despite the fact such an approach is not a U.S. Food and Drug Administration (FDA)-approved indication and has not been shown to improve survival in localized prostate cancer. Adequate evidence shows that androgen deprivation therapy for localized prostate cancer is associated with erectile dysfunction (in approximately 400 of 1000 men treated), as well as gynecomastia and hot flashes.

As discussed above, there is convincing evidence that PSA-based screening leads to substantial over-diagnosis of prostate tumors. As a consequence, there is a high propensity for physicians and patients to elect to treat most cases of screen-detected cancer, notwithstanding the current inability to distinguish tumors that will remain indolent from those destined to be lethal. Thus, many men are being subjected to the harms of treatment of prostate cancer that will never become symptomatic. Even for men whose screen-detected cancer would otherwise have been later identified without screening, most experience the same outcome and are, therefore, unnecessarily subjected to the harms of treatment for a much longer period of time. Such PSA-based screening for prostate cancer has resulted in considerable overtreatment and its associated harms, and the United States Preventative Services Task Force (USPSTF) has considered the magnitude of these treatment-associated harms to be at least moderate. The fact that approximately 70% of prostate core biopsy results are negative also indicates that current non-invasive indications for biopsy (typically elevated PSA and DRE) are not specific for prostate cancer and cause many men to undergo unnecessary biopsy procedures and endure the pain and discomfort associated herewith, as previously discussed.

III. Attempts to Diagnose Prostate Cancer Via Detection of Free Cells

The use of exfoliated prostatic epithelial cells in semen and urine to detect prostate cancer has been reported. See, e.g., Couture, et. al. The isolation and identification of exfoliated prostate cells from human semen. Acta Cyto., 1980 May-June; 24(3): 262-267; Barren et al. Method for Identifying Prostate Cells in Semen Using Flow Cytometry, The Prostate, 1998 August; 36:181-188, Andrade-Rocha. Assessment of exfoliated prostate cells in semen: relationship with the secretory function of the prostate. Several researchers have reported, however, that attempts to detect prostate tumor cells in these specimens routinely is thwarted by unacceptably low sensitivities due to the rare numbers of prostate cells found in the urine. See, Nakai et al., Photodynamic diagnosis of shed prostate cancer cells in voided urine treated with 5-aminolevulinic acid, BMC Urology 2014, 14:59.

In efforts to enhance diagnostic sensitivity, the prior art has employed cell sorting methods or immunomagnetic isolation of prostate cells to enrich the prostate cell population. However, using these cell concentration techniques also failed to provide adequate cell numbers and diagnostic sensitivity. Studies have reported sensitivities ranging between 15% and 30% even when DRE is used to exfoliate prostate cells prior to collection of voided urine. See, Fujita K, Pavlovich C P, Netto G J, et al., Specific detection of prostate cancer cells in urine by multiplex immunofluorescence cytology, Hum Pathol. 2009; 40:924, [PubMed: 19368959]. Furthermore, when found cytologically, PCa cells in the urine occur almost exclusively in patients with high grade or advanced cancers (Tyler K L, Selvaggi S M., Morphologic features of prostatic adenocarcinoma on Thin-Prep® urinary cytology, Diagn Cytopathol. 2011; 39:101. [PubMed: 20146303]).

Although exfoliated prostatic epithelial cells can be acquired by non-invasive or minimally invasive sample collection methods, the potential for use as a reliable diagnostic method for detection of prostate cancer has not been realized due to the low numbers of prostate cells available even following prostatic massage. Indeed, despite efforts to develop devices operative to facilitate collection of samples that seek to improve the probabilities that target cells of interest can be isolated and detected, such devices have proven ineffective. Exemplary of such devices include several intra-urethral devices that are operative to extend into the prostatic urethra and obtain samples in proximity thereto and include those disclosed in Published United States Patent Application Number US2002/0026209, filed in the name of Hung, entitled METHOD AND DEVICE FOR OBTAINING PROSTATIC MATERIAL, published Feb. 28, 2002; Published United States Patent Application Number US2005/0054994, filed in the name of Cioanta, et al., entitled CATHETERS WITH SUCTION CAPABILITY AND RELATED METHODS AND SYSTEMS FOR OBTAINING BIO-SAMPLES IN VIVO, published Mar. 10, 2005; and Published United States Patent Application Number US2011/0208022, filed in the name of Brawer, et al., entitled DEVICE AND METHODS FOR SAMPLING PROSTATIC FLUID, published Aug. 25, 2011, the teachings of all of which are expressly incorporated herein by reference.

Among the drawbacks associated with all such devices and collection techniques using the same include the inability to selectively deploy such devices in a manner that maximizes the potential to capture the target cells of interest at the target prostatic urethral site. Indeed, the use of such devices is completely random and there is no way to determine, and much less selectively deploy such devices at a time when the probability of collecting target cancer cells of interest is greatly enhanced. There is likewise no type of means for maximizing the probability that the target cancer cells will be in the prostatic urethra, as opposed to being located deep within the prostate, as illustrated in FIG. 5, and thus incapable of being accessed by such devices. Accordingly, despite being slightly less invasive, such devices at best only provide a moderately increased chance of detecting the target cancer cells of interest.

A yet further approach is disclosed in published United States Patent Application Number US2009/0263799, filed in the name of Smith et al., entitled ASSAY FOR PROSTATE CANCER, published Oct. 22, 2009. The Smith application proposes the use of Expressed Prostatic Secretion (EPS) as specimens for the detection of prostate cancer. More specifically, various and multiple biomarkers present in the EPS sample are used to determine whether the patient has prostate cell proliferative disorder (prostate cancer, prostate carcinoma, or prostate neoplasm). Smith's method relies on the presumption that prostate cells are the source (origin) of the biomarkers; however, Smith does not include an enumeration or examination of intact prostatic epithelial cells allegedly the source of the biomarkers. Smith likewise does not anticipate the use of an exfoliating agent to increase the sensitivity of the biomarker assay.

In summary, prior art non-invasive and minimally invasive diagnostic methods rely on the supposition that the clinical specimen (peripheral blood, urine, semen, expressed prostatic secretions, etc.) contains a biomarker, genetic material, and/or cells originating from the prostate. The success or failure of prior art detection techniques hinges on the presence of the biomarker, genetic material, or prostate cells in quantities sufficient for detection. The prior art, however, is completely deficient in any sort of structured methodology that can substantially increase the probability that the sought after biomarker, genetic material, or prostate cells can be increased in population and density so as to more easily, readily and accurately assess a patient's condition.

Accordingly, there is an overwhelming need in the art for methods that can be deployed to enhance the ability to collect and detect target prostate cells in a manner that is reliable and readily reproducible, and enables the collected cells to be subsequently tested or otherwise utilized for a wide variety of applications. There is a further need in the art for such methodologies that substantially minimize, if not eliminate, the pain, complexity and numerous other drawbacks associated with needle biopsy procedures while at the same time providing substantially more accurate and sensitive sampling that can detect the presence of a biomarker, genetic material or prostate cell presence to a far greater degree than prior art procedures. Still further, there is a need in the art for such methodologies that are minimally invasive, substantially minimize patient discomfort, have no side effects associated with risk of infection, scarring and debilitating side effects associated with conventional testing and that can be readily deployed on demand without any type of specialized medical equipment, any type of procedure that must be performed by highly trained medical personnel or is otherwise associated with a high cost medical procedure.

BRIEF SUMMARY

The present invention specifically addresses and alleviates the above-identified deficiencies in the art. In this regard, the present invention is directed to minimally invasive methods for generating, collecting and detecting target prostate cells or other biomarkers, genetic material or other compounds related to the condition of prostate cancer as expressed by such cells, such that the presence of such items is greatly enhanced and capable of being more easily, readily and predictably collected for testing purposes than prior art methods. In its broadest terms, the methodology is comprised of two essential components, namely: 1) the administration of an agent that is operative to facilitate, enhance, promote or otherwise cause abnormal and normal cells present in the prostate to become detached or dislodged, such as through a shedding or exfoliating-type action, and migrate through the prostatic urethra epithelial cells and into the urethra; and 2) collecting those cells that have migrated into the urethra for subsequent testing.

With respect to the former, it is contemplated that any of a variety of agents may be administered according to a prescribed dosing regimen in an amount effective to promote the dislodging effect, via a shedding or exfoliation activity for example. Such agents include Dutasteride, Bexlosteride, Izonsteride, Epristeride, Lapisteride, Tursteride, FCE 28260, Zinc, *Serenoa repens* (Saw Palmetto) extract, *Pygeum africanum* extract, Nettle Root extract, Lycopene, Green Tea catechins (including, but not limited to: (−)-epigallocatechin, (−)-Epigallocatechin-3-gallate, and (−)-Epicatechin), Polyphenon E, Theaflavins, Dietary Isoflavones (including: genistein, daidzein, formononetin, and biochanin A), Curcumin, Reservatrol ((3,5,4')-trihydroxystilbene), Pomegranate juice, and Lupeol. The most ideal candidates would be considered those agents having a debulking-type activity, as occurs with the 5-alpha reductase inhibitor class of drugs, which includes Finasteride. Common to all such agents, however, is the ability of the administered agent, when administered in an effective amount to permeate through vascularization of the prostate and facilitate a dislodging, detaching, shedding, or exfoliating-type action throughout the entirety of the prostate to thus ultimately cause the migration of target cells through prostatic ducts and into the urethra so as to obtain an optimal, fully-inclusive sampling of the prostate, as oppose to the sampling of minute quantities of prostatic tissues as occurs with needle biopsy.

Such agents may be given alone or in combination with one or more other agents and as a single dose or multiple doses over time, according to a prescribed dosing regimen, so as to promote a sampling "window" when an optimal degree of suspected target cells will have migrated into the patient's urethra. Along those lines, it is contemplated that a specific window of time following administration of a specific agent will correspond to a time when the target cells of interest are more likely to be present in greater concentrations within the urethra and available to capture as part of a sample or specimen. For example, in the case of Finasteride, it is contemplated that 5 mg/day dose will produce an especially good degree of shedding, and hence a heightened population of target cells within the urethra, beginning approximately 72 hours from administration and persisting for up to six months or approximately 180 days. In some instances, it is contemplated that a single Finasteride dose ranging from 80 mg to 600 mg may be administered. In other instances, it is contemplated that daily Finasteride dosages may range from 5 mg/day to 80 mg/day. It is believed that the first 30 days may produce especially good target cell populations for collection. Other examples include a combination dosage of 5 mg/day to 80 mg/day Finasteride and 4 mg/day to 8 mg/day Doxazosin, which will produce an especially good sampling "window" approximately beginning 72 hours after administration and continue for another 30 days or more.

Empirical methods may be used as an alternative to time-based determination of the optimum sampling "window." For example, a reduction in prostate volume, as determined by palpation or by visual inspection, MRI or ultrasound, may be used as a determinative event as to when a specimen should be collected. Additionally, a rise or drop in the concentration of a biomarker that is associated with the prostate debulking process may signal an optimum window for sample collection. In all such applications, it will be appreciated that the administration of a given agent or combinations thereof will culminate in an optimum opportunity where the number and concentration of target cells sought to be collected can be selectively produced and made available for capture.

To facilitate the ability of the agent to produce a shedding or exfoliating phenomenon, it is contemplated that the agent may be supplemented with a second administered agent or mechanical manipulation, such as prostatic massage, vibration, ultrasound and the like, to thus complement the shedding or exfoliating action of the administered agent. Such application of mechanical forces will likewise preferably be selectively timed so as to enhance the ability of the target cells to be dislodged, detached, shed or exfoliated at a predictable time that will coincide with optimal sample collection. Such complementary mechanical forces may be applied through any of a variety of techniques well-known in the art.

It is also contemplated that some patients who are being treated for benign prostate hypertrophy (BPH) and have been placed on a 5-alpha reductase inhibitor, and in particular Finasteride or other similar BPH therapies for six (6) months or more, may have less target cell shedding and it may be necessary to remove the patient from such therapy in order, to regrow target cells susceptible to shedding. The "off-therapy" period may be fixed or determined empirically. For example, an increase in prostate volume as determined by palpation or by visual inspection by MRI or ultrasound may be used to determine when the agent can be re-administered. Additionally, a rise or drop in the concentration of a biomarker that is associated with the prostate bulking process may signal when target cells have sufficiently replenished for harvesting. Once confirmed, the patient may be placed back on therapy to produce exfoliation of target cells.

With respect to the second aspect of the invention, namely, sample collection, it is contemplated that the target cells of interest caused to migrate into the urethra can be removed therefrom through simple specimen collection. Presently, it is contemplated that any of a variety of types of specimens can be collected to obtain the ideal sample for testing. However, it is believed that a hierarchy of types of specimens as collected per the methods of the present invention exist and can be ranked according to the likelihood a given specimen will have the highest concentration of target cells of interest. In this regard, it is believed that an ejaculate specimen collected at a time coinciding with an optimal sampling "window" would provide the best specimen for testing in terms of the number and concentration of target cells. Following an ejaculate specimen collected during the optimal "window", the following other specimens are ranked according to their respective probabilities of containing a maximum amount of target cells sought to be tested from greater to lesser effectiveness: expressed prostatic secretions (EPS); internal prostatic massage followed by urine void; external prostatic massage followed by urine void; digital rectal examination followed by urine void; and lastly, urine void only. Again, each type of sample will be obtained at an interval where the agent administered to the individual has caused the target cell population to be shed, exfoliate, etc. into the urethra at a maximum rate or concentration.

Once collected, the sample may be tested by any of a variety of conventional means for any of a variety of analytes of interest, whether they be cancer cells, biomarkers, genetic material such as PSA, CtDNA, mRNA, microRNA, exosomes, and other materials known and sought out for testing as understood in the art. However, by selectively increasing the number and concentration of cells of interest, as well as using a minimally invasive method for collecting the target cells and other biological materials related thereto in a manner that minimizes patient discomfort and instead relies upon natural biological mechanisms, the methods of the present invention can obtain superior test samples in a far easier, much less painful and substantially more cost-effective manner than prior art methods. Moreover, because of the enriched nature of the samples collected by the methods of the present invention, it is believed that such methods will produce samples that provide substantially more accurate results, as well as results that can possess greater sensitivity than methods relying upon random sampling that do not otherwise increase the probability that such target cells of interest can be selectively and optimally obtained at a specific time.

As will be readily appreciated by those skilled in the art, the methods discussed herein to obtain optimal samples and the subsequent testing of the enriched samples can be for a variety of purposes, such as detecting prostate cancer in asymptomatic patients, predicting/measuring prostate tumor susceptibility to drug regimens, active surveillance of patients whose prostate biopsy results are negative (yet continue to exhibit symptoms consistent with prostate cancer) and identifying false-positive results associated with biomarker assays, among others. In one specific application believed to be of great significance, the methods of the present invention can be utilized to detect high-grade prostatic intraepithelial neoplasia (PIN), which is widely recognized as the pre-invasive stage of adenocarcinoma in the prostate and regarded as a highly predictive marker of adenocarcinoma.

It is therefore an object of this invention to provide a method that uniformly samples epithelial cells from the entire prostate gland.

It is a further object of this invention to provide a method for active surveillance of men with persistent indications of prostate cancer.

It is a further object of this invention to provide a method for non-invasive exfoliation and isolation of morphologically correct prostatic epithelial cells in sufficient quantity to allow for identification and interrogation of said prostate cells by any combination of molecular, immunochemical, and physical analytical methods.

It is a further object of this invention is to administer a therapeutic or other agent that accelerates exfoliation (shedding) of prostate cells for the purpose of increasing the number of prostate epithelial cells available for detection in body fluids including (but not limited to) urine, semen, and expressed prostatic secretions.

Another objective of this invention is to provide a non-invasive method for screening for prostate cancer to facilitate identification of individuals with high grade PIN by exfoliating the prostatic epithelial cells.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
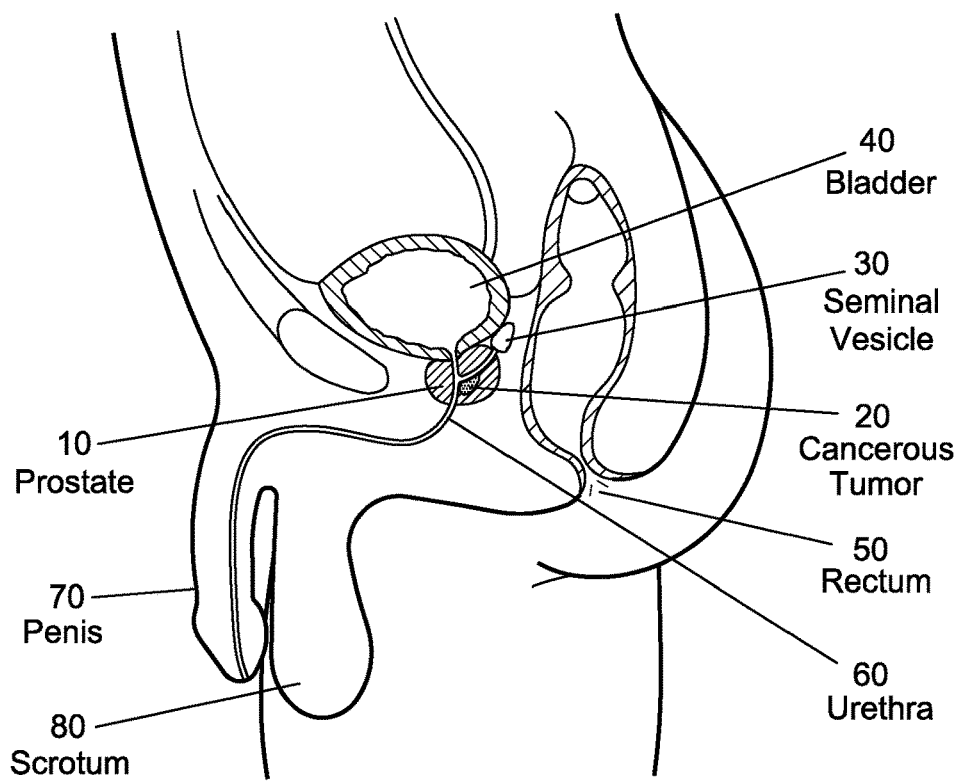
FIG. 1 is a side, partial cross-sectional view of a prostate having a cancerous tumor therein, and the surrounding organs and male reproductive system.
Figure 2:
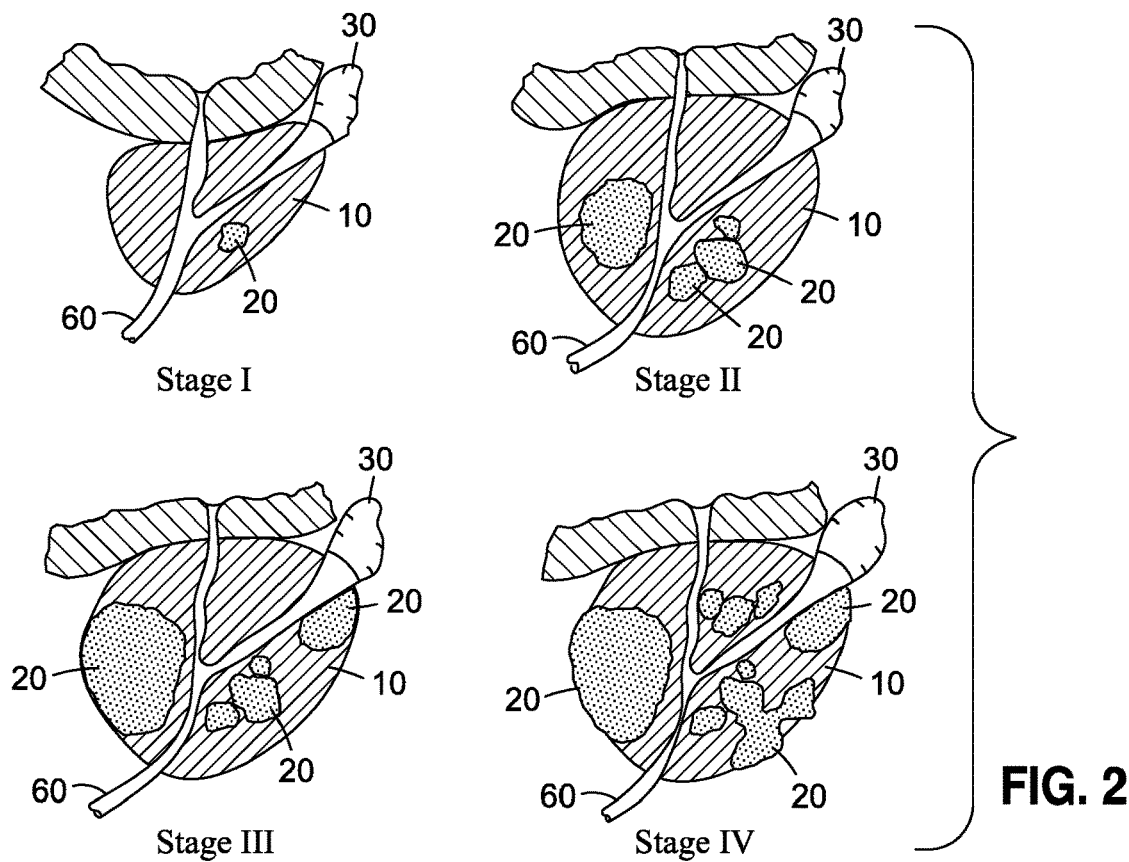
FIG. 2 is a cross-sectional view of a cancerous prostate corresponding to Stages I to IV.

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention.

In this regard, the present invention is directed to methods for facilitating the ability of prostatic epithelial cells situated in the prostate to become dislodged from the prostate and migrate into the urethra for subsequent collection. The methods of the present invention are thus operative to generate a greater population of prostatic epithelial cells to be more readily collected and detected for any of a wide variety of uses, including differentiating between BPH and prostate cancer, predicting or measuring prostate tumor susceptibility to drug regimens, monitoring and identifying any pre-cancerous activity, and identifying false-positive results associated with biomarker assays, as is well-recognized in the art. Such target cells, which are generally characterized as prostatic epithelial cells, can be, for example, normal, hyperplastic, atypical, neoplastic, malignant, and other types well-known in the art. Of particular interest, the methods of the present invention are believed to have exceptional effectiveness in the detection of high-grade prostatic intraepithelial neoplasia (PIN), which is regarded as a highly predictive marker of adenocarcinoma and most likely the pre-invasive stage of adenocarcinoma in the prostate.

To achieve these objectives, the present invention is operative to deploy a first step, which comprises the administration of an agent operative to facilitate the dislodgement of the target prostatic epithelial cells from the prostate, which may be through such mechanisms as shedding, exfoliation, and the like, and the subsequent migration of those cells into the urethra. Such initial step, discussed more fully below, is essentially accomplished via the administration of an agent, which is operative to effectuate the cellular dislodgment of the prostatic epithelial cells from prostatic ducts.

In a second step, the cells that migrate into the urethra from the prostatic ducts are then collected, preferably non-invasively, as a fluid specimen, such as an ejaculate or urine void. The collection of such specimen will be coordinated with the administration of the agent such that the timing of the specimen collection will coincide to when an optimum sample "window" will occur whereby the population of prostatic epithelial cells induced to dislodge, shed or exfoliate and migrate into the urethra will reach a maximum population or density so as to increase, and preferably substantially increase, the number of those cells sought to be identified and characterized. To facilitate that objective, it is contemplated that, optionally complementary forces, such as the application of a mechanical force, vibration, prostatic massage, and the like, may be deployed so as to enhance the ability of the cells to become dislodged and migrate into the urethra, so as to promote the effectiveness of the administered agent, as well as to enable such cells to be more readily accessed during sample collection. Each of these specific aspects is discussed below.

Figure 3:
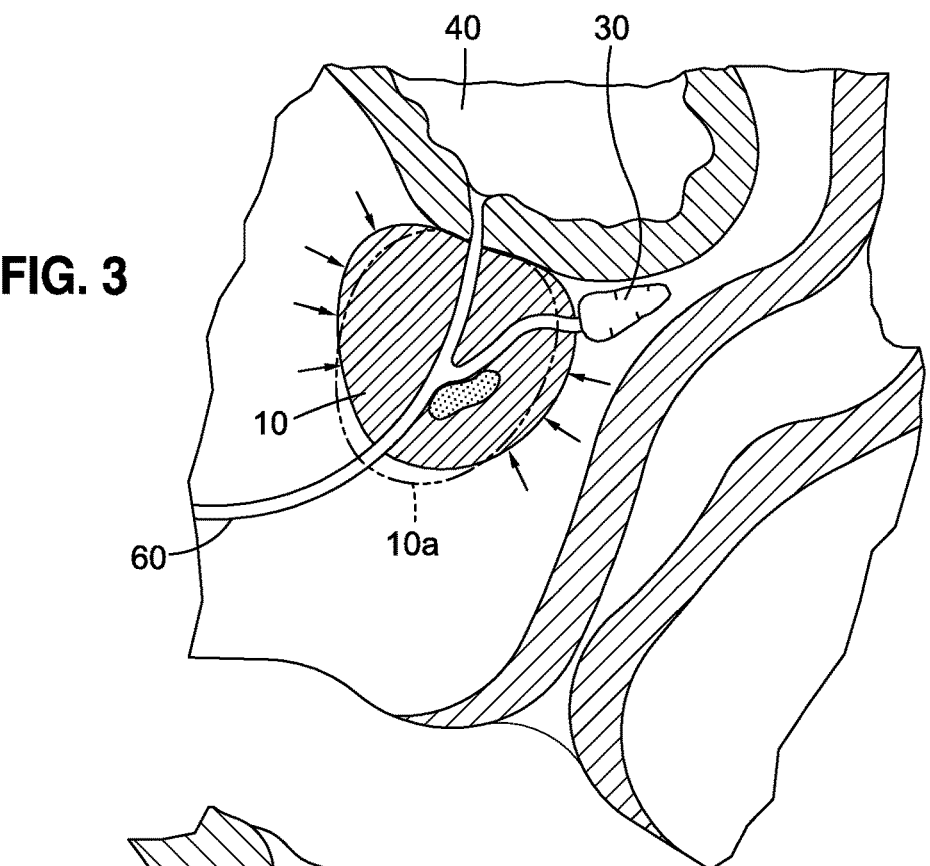
FIG. 3 is a cross-sectional view of a prostate having a cancerous tumor and urethra extending therethrough as saturated below the bladder, the prostate shown as transitioning from a native state to a debulking state, the latter shown in phantom.
Figure 4:
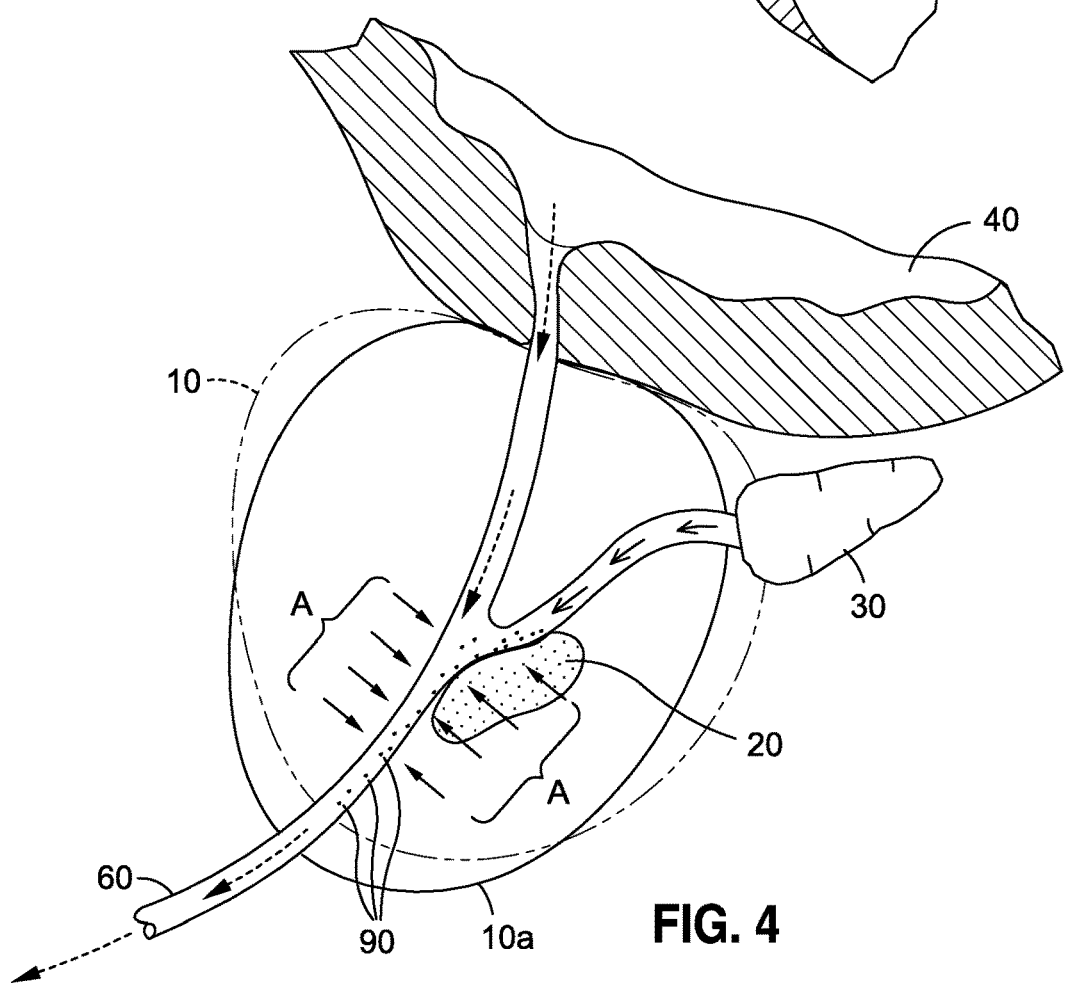
FIG. 4 is the cross-sectional view of FIG. 3 wherein the prostate is shown in its native state, in phantom, and in a debulking state, shown in solid line, wherein debulking configuration is shown being operative to cause cells from the tumor contained within the prostate to shed into the urethra for extraction.

I. Administration of Agents to Facilitate the Collection of Prostatic Epithelial Cells The present invention expressly contemplates an "agent" that will be ingested by, or otherwise systemically administered to, a male individual from which a sample of target cells is sought to be derived and examined. To that end, such agent may take any of a variety of compounds, discussed more fully below, that is operative to cause the dislodgment of target prostatic epithelial cells and or their contents (e.g., DNA, mRNA, exosomes, etc.) from the prostate and ultimately into the urethra for collection. The general process by which such activity is accomplished is depicted in FIGS. 3 and 4 that illustrate an exemplary mechanism by which the objectives of the present invention are accomplished. As illustrated in FIG. 3, the administration of the agent will be operative to impart an effect, illustrated by the inwardly-directed arrows about the prostate 10, that will cause the prostate in its native shape and configuration 10 to transition to a debulking state, shown as 10*a* in phantom. In this regard, the agent administered to the male individual, via the delivery of the agent through the vasculature of the prostate 10, imparts the debulking affect, shown as 10*a*. Advantageously, the debulking effect is effectuated throughout the entirety of the prostate 10 so that prostatic epithelial cells distributed throughout the prostate are all susceptible to the dislodgement, shedding, or exfoliating action, as opposed to the random chance such cells may be captured through needle biopsy. Accordingly, the present invention thus enables target prostatic epithelial cells to be potentially obtained anywhere throughout the prostate, which has never before been accomplished as a mechanism for deriving such cells.

As a consequence of the debulking activity of the agent, there is shown in FIG. 4 the subsequent effects whereby the action of the agent is shown permeating through the prostate, as indicated by the arrows designated as "A," such that the effects of the agent cause target protastic epithelial cells located within the tumor to become dislodged therefrom and migrate into the urethra 60, and characterized as free cells 90. With respect to the mechanism by which an agent accomplishes such dislodgement, followed by migration into the urethra, it is contemplated that any agent operative to produce such effect will be deemed within the scope of the present invention. In this regard, it is contemplated that the agents deployed in connection with the present invention may impart a dislodging effect via such mechanisms as cellular shedding or exfoliation, among others, that would be understood by those skilled in the art.

It is further contemplated that the optimal degree of cellular dislodgment and migration from prostatic ducts and into the urethra may be selectively timed following the administration of a particular agent so as to precisely time the collection of a specimen, discussed more fully below, at an interval or "window" that maximizes the probability that a sample can be collected having a maximum number of target abnormal cells to be identified. With respect to exemplary agents for use in the practice of the present invention, such agents include but are not limited to: Dutasteride, Bexlosteride, Izonsteride, Epristeride, Lapisteride, Tursteride, FCE 28260, Zinc, *Serenoa repens* (Saw Palmetto) extract, *Pygeum africanum* extract, Nettle Root extract, Lycopene, Green Tea catechins (including, but not limited to: (−)-epigallocatechin, (−)-Epigallocatechin-3-gallate, and (−)-Epicatechin), Polyphenon E, Theaflavins, Dietary Isoflavones (including: genistein, daidzein, formononetin, and biochanin A), Curcumin, Reservatrol ((3,5,4')-trihydroxystilbene), Pomegranate juice, and Lupeol. The dosage, route of administration and approximate interval of time from when a given agent is administered to when the desired target cells migrate into the prosthetic urethra for optimum collection (i.e., the drug latency period from when the administered agent is applied to a biologic system and the time at which the specified pharmacologic effect is produced), can be determined by one of ordinary skill using conventional time-dose curve analysis and measuring and quantifying dose-dependent physiological effects over time. Accordingly, the dosage of such agents, how such agents are preferably administered, and the approximate time following the administration of each respective agent to when the maximum number of cells of interest are caused to be dislodged and migrate into the urethra so as to coincide with an optimal sampling "window," are thus deemed within the skill of the ordinary artisan.

In addition or as an alternative to a time-dependent determination when the optimum degree of target cell collection occurs relative the administration of an agent, it is further contemplated that optimal sample collection may be determined based upon a corresponding physiological event following the administration of an agent. For example, optimal target cell collection following the administration of a given agent may coincide with physiological changes of the prostate. In particular, to the extent certain physiological changes are manifested by the prostate following the administration of an agent that are indicative of a debulking condition, the timing of sample collection may coincide with such physiological changes. For example, to the extent physiological changes in the prostate can be determined, such as through palpitation, visual inspection or an imaging modality such as MRI or ultrasound, sample collection coinciding with such physiological changes following the administration of an agent will thus be indicative of a "window" for optimum sample collection.

Similarly, the presence of one or more biomarkers following the administration of an agent may signal an optimum sample collection opportunity. For example, to the extent PSA levels are shown to drop to a certain level following the administration of one or more agents can thus be deemed indicative of when epithelial prosthetic cells have been caused to shed, dislodge and the like and migrate through prosthetic ducts and into the urethra for subsequent collection, discussed below. Accordingly, using techniques well-known to those skilled in the art, it is contemplated that a dose-dependent change in the presence of a particular biomarker can thus coincide with optimum sample collection.

As will further be appreciated, it is believed that combinations of such methods to secure optimum target cell collection following the administration of an agent may be deployed. For example, it is contemplated that a certain time interval following the administration of an agent may be coupled with measuring a decrease in a biomarker, such as PSA levels, such that a certain duration following the administration of an agent, coupled with documented decrease in PSA levels will thus define an optimum sample collection opportunity. Likewise, following a certain duration following the administration of an agent, the prostate may be examined, such as through palpitation and the like, and upon certain documented changes in the physiological condition of the prostate indicative of shedding, exfoliating activity or the like, will thus be indicative as to when an optimal collection of cells should be made.

Exemplary of such agents classified as 5-alpha reductase inhibitors either synthetic or naturally occurring (Ref: Khan et al., Apoptosis by dietary agents for prevention and treatment of prostate cancer, Endocr Relat Cancer, 2010 March; 17(1): R39-R52) are well-known and extensively utilized for therapeutically reducing the mass of prostate tissue (Ref: Johnson U.S. Pat. No. 5,496,556) (Ref: Wikipedia 5-alpha-reductase inhibitor, Jan. 20, 2016). Engel et al. have shown that prostate volume decreases (tissue debulking) between 20% and 40% can occur in a treatment time of 4 to 8 weeks (U.S. Pat. No. 6,054,432). Similar findings have been noted in numerous clinical studies involving 5-alpha reductase inhibitors used alone or in combination with other agents (Smith et al., Therapeutics and Clinical Risk Management 2009:5 535-545). As will be appreciated by those skilled in the art, this is a volume of prostate tissue far exceeding the amount of tissue that is acquired using prostate core needle biopsy. Finasteride (sold under the trademark Proscar®) is routinely prescribed for the treatment of benign prostatic hyperplasia. In a study investigating the use of 5-alpha reductase inhibitors for chemoprevention of prostate cancer, the authors concluded that long term use of finasteride decreased the risk of low-grade prostate cancer (Ref: Thompson et al., Long-Term Survival of Participants in the Prostate Cancer Prevention Trial, N Engl J Med 2013; 369:603-610). Despite the well-known benefits of 5-Alpha reductase inhibitors and other agents to exfoliate prostate cells for therapeutic purposes, the use of these same agents to exfoliate prostate cells for diagnostic purposes has not been reported.

For purposes of practicing the present invention, a single dose of 80 mg to 600 mg of Finasteride will produce a good degree of shedding activity, corresponding to a heightened population of target cells within the urethra, following approximately 72 hours from administration. Alternatively, it is believed that a daily dosage from 5 mg/day to 80 mg/day of Finasteride will produce an especially good degree of shedding activity corresponding to a heightened population of target cells within the urethra, following approximately 72 hours from administration. It is believed that continuous 5 mg/day dosage therapy over a maximum of six months will provide a continuous shedding activity and thus enriching the target cell population sought to be collected. It is believed that 30 days of such therapy may produce a sufficient degree of shedding over time so as to generate an especially good number of cells sought to be collected. In another application, it is believed that a combination of first and second agents can be administered to produce the desired degree of shedding. Exemplary of such administration of first and second agents include administering Finasteride, as a first agent from between 5 mg/day to 80 mg/day along with Doxazosin as a second agent, administered from between 4 mg/day to 8 mg/day. Such combination of administered agents will produce an especially good sampling "window"

Androgen blockers such as Flutamide can likewise cause precancerous epithelial cells to shed into the urethra. Such class of drugs may be particularly suited to facilitate the dislodgement and collection of PIN which can precede elevation of PSA. Such approach is believed to enable the earliest possible method to detect or predict prostate cancer, ever before elevated levels of PSA are found. Indeed, a prostate core biopsy is not indicated until an elevated PSA result is obtained.

In fact, in certain applications of the present invention, it is contemplated that patients already on 5-alpha reductase inhibitor therapy may necessarily need to discontinue such therapy until such time as the shedding-induced activity attendant to taking such inhibitors ceases within the individual to be tested. Along those lines, to obtain a sample whereby the target cells are believed to be most populous and highest in concentration may require a cessation of any on-going shedding or exfoliating activity produced by such inhibitors. By waiting a sufficient duration until such time as the shedding or exfoliating activity ceases, the cell population will be able to rebuild and accumulate such that when a 5-alpha reductase inhibitor is reintroduced into the individual, a maximum number of prosthetic cells will be available for subsequent "harvesting" since a greater degree of such cells will be present and available for shedding and subsequent detection than would occur in the individual on maintenance therapy with such inhibitors. Indeed, to the extent such cell population were not allowed to re-bulk, in certain applications, such as the administration of Finasteride that would cause PIN cells to shed, optimum cell detection may be inhibited.

II. Subsequent Sample Collection

As illustrated in FIG. 4, the target cells of interest 90, by virtue of being situated within the urethra 60, are thus optimally positioned for non-invasive collection. In this regard, by virtue of the cells 90 being positioned downstream from bladder 40 and seminal vesicle 30, such target cells 90 are thus downstream from such fluid sources and advantageously positioned to be carried thereby and out of the body through the urethra 60. As will be readily appreciated by those skilled in the art, by virtue of being able to collect samples having a maximum degree of target cells of interest in a manner that is not only minimally invasive but also eliminates all the drawbacks associated with prior art detection practices, is a substantial advancement over the prior art. Indeed, the ability to collect a non-invasive sample not only eliminates all the substantial drawbacks associated with needle biopsy practices, but also enables samples to be collected that are far more abundant in target cells, readily reproducible, and can possess a substantially greater sensitivity given the selective ability of the methods of the present invention to create and selectively time the collection of the sample that coincides with when a target cell population reaches a maximum or near-maximum concentration within the urethra.

With respect to the sample collection that is envisioned by the present invention, it is contemplated that any biological samples that can be collected through a patient's urethra is deemed within the scope of the present invention. Exemplary of the types of specimens that can be collected in the practice of the present invention include ejaculate, EPS (Express Prostatic Secretions), urine void preceded by internal prostate massage, urine void preceded by external prostate massage, urine void preceded by digital rectal examination, and urine void only.

As discussed above, the collection of any of the foregoing specimens will preferably be coordinated to coincide with the optimal sample collection "window" following administration of a given administered agent. In all such methods of sample collection, however, it is believed that any prior art techniques can be utilized and any collection methods in use or later developed are deemed to be within the scope of the present invention.

Figure 5:
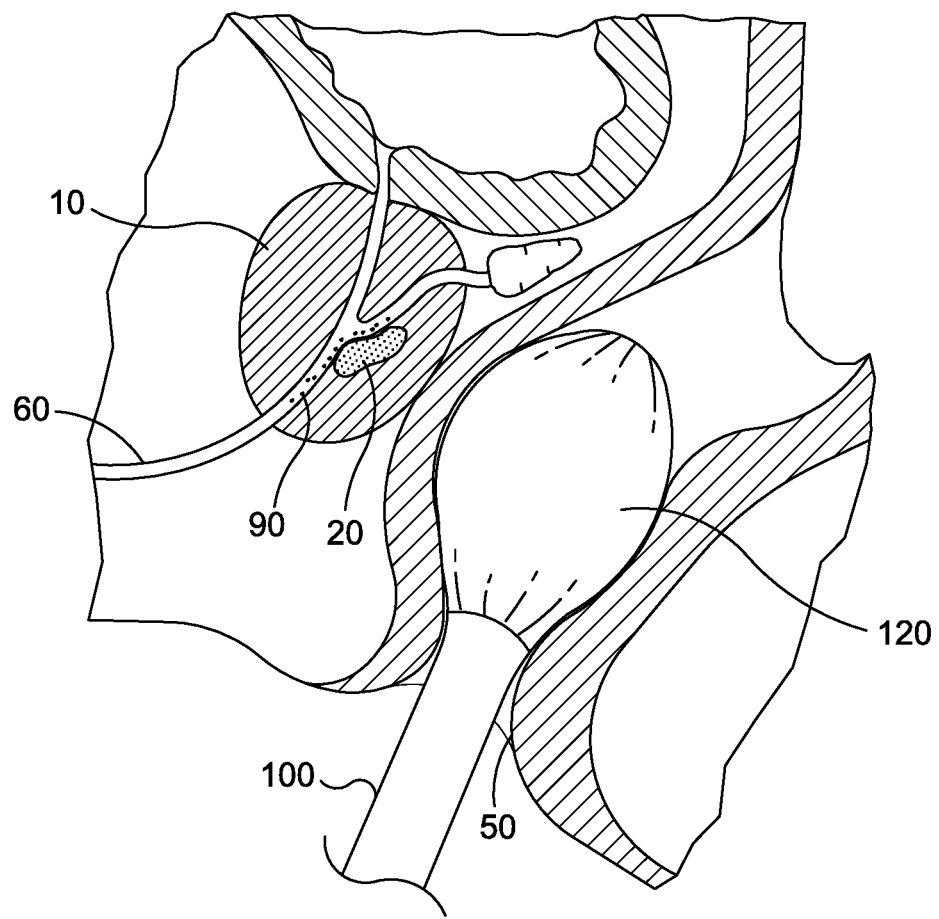
FIG. 5 is a cross-sectional view of a prostate and cancerous tumor situated in the anterior of the prostate wherein there is further depicted a mechanical mechanism deployed through the rectum and adjacent the prostate for use in facilitating the transfer of cells from the tumor to the urethra for extraction.

In optional variations of the present invention, it is believed that two or more agents may be administered prior to sample collection to the extent multiple agents can further enhance the population of abnormal target cells to dislodge, shed, exfoliate, or the like and migrate into the urethra to the maximum extent possible. To that end, it is expressly recognized that the administration of such agents and subsequent sample collection will be selectively chosen so as to maximize the cell population sought to be collected within the sample. Likewise, as depicted in FIG. 5, it is contemplated that a complementary mechanical force or stimulation may be deployed in combination with an agent and subsequent sample collection so as to maximize the presence and subsequent collection of atypical cells in the urethra. In the exemplary embodiment shown in FIG. 5, an instrument 100 having a pressure exerting mechanism 120 is inserted through the rectum and positioned adjacent the prostate 10 and operative to impart a compressive force thereto so as to facilitate the dislodgment of cells from the tumor 20 disposed deep within the prostate 10 and ultimately as free cells 90 in the urethra 60. In this regard, pressure exerting mechanism 120 may impart a massaging-type force, similar to prostatic massage, or may deploy other mechanical forces, such as vibrational energy, ultrasound, RF energy, heat or any of other of a variety of mechanical forces and/or energy, as well as combinations thereof, that further operate to facilitate cellular dislodgment and migration from a tumor 20 into the urethra 60. Along those lines, it is believed that any such external force or energy may be applied either externally or internally, and in a position so as to optimally apply a desired mechanical force or energy to a specific target site upon the prostate.

In all cases, once a suitable specimen has been collected, the specimen may be utilized for any of a wide variety of applications, as described above. For example, the specimens collected through the methods of the present invention can be utilized for post-biopsy chemotherapy surveillance. The present invention likewise can provide a method for effective sampling of the prostate tissue at any frequency required for a diagnosis. The non-invasive nature and potential health benefits of prostate cell exfoliation allow for sequential sampling the patient to support differential diagnosis, whether BPH or cancer. There are also more testing options available than with prior art needle-collected biopsy material that advantageously allows for reflex testing. For example, initial evaluation using AMACR or PAP stain may warrant molecular tests e.g.: Fluorescent In Situ Hybridization, gene array, PCR, NGS, etc.

Also, many genetic abnormalities and biomarkers may have multiple sources and are not specific to cell type. Her2-neu, PTEN, tP53 abnormalities occur in many cancers other than prostate. In PIN (prostatic intraepithelial neoplasia) prostatic epithelial cells can look abnormal under a microscope, and while sometimes the abnormalities are minor, in some cases such cells start to look like the cellular changes characteristic of cancer cells. An object of the present invention is to provide specificity to the cell type, so that the correct origin of the cell can be identified. For example, aneuploidy in cells found in urinary tract can be indicative of bladder cancer, squamous cell carcinoma, kidney cancer, and prostate cancer. These cancers can occur concurrently. Prostate cancer occurs in 30% of men with bladder cancer.

The sample collection methods of the present invention can further be used to confirm positive or negative test results resulting from elevated PSA levels. As is well-known, PSA may be elevated due to UTI, prostatitis, prostate manipulation, sexual activity, etc., and not necessarily attributable to the presence of prostate cancer. The present invention advantageously enables an elevated PSA level to be deemed attributable to cancer or some other causal factor not related to cancer. Numerous other conventional tests that can be utilized as discussed above as well as numerous other applications readily understood by those skilled in the art.

Provided here as an example of an individual prostate health screening kit whose components are used to perform the invention. As envisioned, the kit will contain a package of 10 pairs of exfoliating tablets wherein the 10 pairs of tablets each containing a first tablet containing a quantity of Exfoliating Agent 1 and a second tablet containing a quantity of Exfoliating Agent 2. Also included are a prostatic cradle and a specimen collection container(s). Using the tablets provided in said kit, an individual ingests one pair of said exfoliating tablets once per day for 10 days. 24 hours after ingestion of the tenth (last) pair of first and second exfoliating tablets, said individual positions the prostatic cradle in the groin region in a manner that applies pressure that externally massages the prostate gland when seated. Said individual sits on said prostatic cradle for 15 minutes. After 15 minutes of external prostatic massage an ejaculate specimen is collected in said specimen collection container.

Provided here as second example is an individual prostate health screening kit whose components are used to perform the invention. Per such embodiment, the kit contains a package of 10 pairs of exfoliating tablets is provided. The 10 pairs of tablets each pair containing a first tablet containing a quantity of Exfoliating Agent 1 and a second tablet containing a quantity of Exfoliating Agent 2; a pressure exerting instrument 100; and a specimen collection container(s). Using the tablets provided in said kit, an individual ingests one pair of said exfoliating tablets once per day for 10 days. 24 hours after ingestion of the tenth (last) pair of exfoliating tablets, said individual performs internal prostatic massage using the pressure exerting instrument 100 having a pressure exerting mechanism 120 inserted through the rectum and positioned adjacent the prostate 10 and operative to impart a compressive force thereto so as to facilitate the dislodgment of cells from the tumor 20 disposed deep within the prostate 10 and ultimately as free cells 90 in the urethra 60. After performing said prostatic massage for 5 or more minutes an ejaculate specimen is collected in said specimen collection container.

In either of the prostate health screening kits aforementioned it is contemplated that a voided urine may be substituted for an ejaculate specimen. Likewise, in either of the prostate health screening kits aforementioned it is contemplated that said internal or external massage may be performed with the assistance of a physician or other individual trained in the art of prostatic massage.

Although the methods discussed herein are specifically tailored for application to the prostate, it should be understood that the general principles of administering an agent to facilitate the dislodgment of a target cell of interest and positioning that target cell in a manner for easy, non-invasive collection may find widespread application for a number of different types of cancers or whenever it may be desired to attempt to secure cells that are otherwise difficult to obtain by biopsy and the like. For example, it is believed that the administration of an agent that facilitates cellular dislodgment, whether it be by shedding, exfoliation, or any other mechanism, that is also operative to make available target cells that can be easily accessed, such as cancer cells in the lungs obtained through a sputum sample, or an agent that is operative to dislodge and release a tumor cell situated within a kidney that is excreted into the urine, are further examples that are contemplated to be within the scope of the present invention. Along those lines, it will be understood that the agent so selected will be operative to impart the dislodging effect on the cell of interest in the target organ, whether it be the lung, kidney or other target organ, and further that the timing and/or circumstances associated with the administration of such agent relative to the ultimate sample collection will be selectively determined so as to optimize the number and concentration of cells in a given sample so as to increase the statistical possibility that the target cells of interest can be detected.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A method for isolating and collecting prostatic epithelial cells situated within the prostate of an individual not being treated for benign prostate hypertrophy (BPH), the method comprising the steps:
   a. systemically administering at least one debulking agent to said individual not being treated for BPH in an amount effective to detach said prostatic epithelial cells from within the prostate wherein a portion of said detached prostatic epithelial cells are operative to migrate to the prostatic urethra via prostatic ducts; and
   b. collecting a specimen emanating from the prostatic urethra, said specimen collection corresponding to when said detached prostatic epithelial cells migrate to said prostatic urethra and coinciding with when an increased population of said detached prostatic epithelial cells are present in the prostatic urethra following said administration of said debulking agent in step a).

2. The method of claim 1 wherein said at least one debulking agent comprises a 5-alpha reductase inhibitors.

3. The method of claim 2 wherein said 5-alpha reductase inhibitor comprises Finasteride.

4. The method of claim 3 wherein step b) comprises collecting said specimen at a time from 72 hours to 6 months or more from said administration of Finasteride.

5. The method of claim 1 wherein in step b), said specimen collection comprises collecting an ejaculate from said individual.

6. The method of claim 1 wherein in step b), said specimen collection comprises collecting an express prostatic secretion from said individual.

7. The method of claim 1 wherein in step b), said specimen collection comprises collecting a urine specimen from said individual.

8. The method of claim 7 wherein prior to collecting said urine specimen, an internal prostatic massage is performed upon said individual.

9. The method of claim 7 wherein prior to collecting said urine specimen, an external prostatic massage is performed upon said individual.

10. The method of claim 7 wherein prior to collecting said urine specimen, a digital rectal examination is performed upon said individual.

11. The method of claim 1 wherein step b) comprises collecting said specimen at a time when said prostate assumes a debulking physiological state following administration of said debulking agent.

12. The method of claim 11 wherein the determination of when said prostate assumes said debulking state is made by palpitation.

13. The method of claim 11 wherein the determination of when said prostate assumes said debulking state is determined by visual examination.

14. The method of claim 11 wherein the determination of when said prostate assumes said debulking state is determined by an imaging modality selected from the group consisting of MRI and ultrasound.

15. The method of claim 1 wherein step b) comprises collecting said specimen at a time corresponding to when a biomarker is present in a concentration indicative of when said prostate assumes a debulking physiological state following administration of said debulking agent.

16. The method of claim 15 wherein said biomarker consists of PSA and wherein said PSA is present in a concentration indicative as to when said prostate assumes said debulking state.

17. The method of claim 4 wherein step b) comprises collecting said specimen at a time from 72 hours to 30 days from said administration of Finasteride.

18. The method of claim 3 wherein said Finasteride is administered in a dose ranging from 5 mg/day to 8 mg/day.

19. The method of claim 18 wherein said Finasteride is administered in a dose of 5 mg/day.

20. The method of claim 1 wherein step a) comprises administering Finasteride and Doxazosin.

21. The method of claim 1 wherein step a) comprises administering a single dose of Finasteride ranging from 80 mg to 600 mg.

* * * * *